(12) United States Patent
Andre et al.

(10) Patent No.: US 7,718,203 B2
(45) Date of Patent: May 18, 2010

(54) PROTECTING AND REGENERATING COMPOSITION

(75) Inventors: Patrice Andre, Neuville Aux Boix (FR); Isabelle Renimel, Trainou (FR)

(73) Assignee: LVMH Recherche, Saint Jean de Braye (FR)

( * ) Notice: Subject to any disclaimer, the term of this patent is extended or adjusted under 35 U.S.C. 154(b) by 73 days.

(21) Appl. No.: 11/668,912

(22) Filed: Jan. 30, 2007

(65) Prior Publication Data
US 2007/0243148 A1  Oct. 18, 2007

(30) Foreign Application Priority Data
Feb. 3, 2006  (FR) .................................. 06 50400

(51) Int. Cl.
*A61K 36/87* (2006.01)
(52) U.S. Cl. .......................... 424/766; 424/401; 424/74
(58) Field of Classification Search .................. 424/401, 424/766, 74
See application file for complete search history.

(56) References Cited
U.S. PATENT DOCUMENTS

| | | | | |
|---|---|---|---|---|
| 5,789,414 A | * | 8/1998 | Lapidot et al. | 514/256 |
| 6,602,514 B1 | * | 8/2003 | Bunger et al. | 424/401 |
| 6,903,134 B2 | * | 6/2005 | Pflucker et al. | 514/470 |
| 2004/0052879 A1 | * | 3/2004 | Ravagnan et al. | 424/762 |
| 2004/0197299 A1 | * | 10/2004 | Delattre et al. | 424/78.02 |

FOREIGN PATENT DOCUMENTS

WO   WO 01/03713 A1   1/2001

* cited by examiner

*Primary Examiner*—Johann R Richter
*Assistant Examiner*—Danielle Sullivan
(74) *Attorney, Agent, or Firm*—Caesar, Rivise, Bernstein, Cohen & Pokotilow, Ltd.

(57) ABSTRACT

The invention relates to a protecting and regenerating composition.

Figure 1:
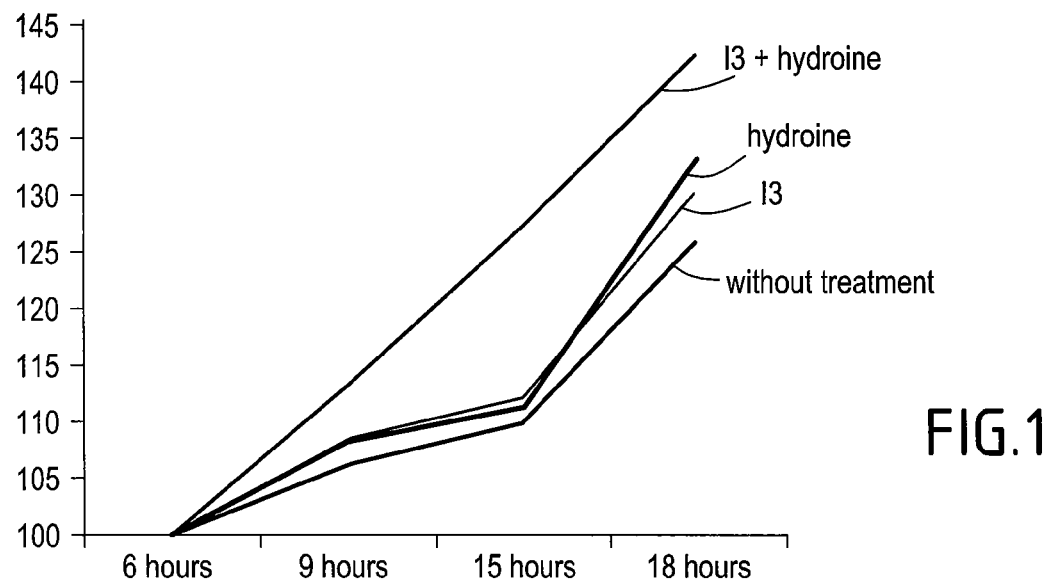

This composition comprises an association of a first cosmetically active ingredient comprising a dried vine shoot extract, and a second cosmetically active ingredient comprising a component of the ectoine type.

This composition makes it possible to affect anti-ageing cosmetic care and skin revitalization.

26 Claims, 1 Drawing Sheet

PROTECTING AND REGENERATING COMPOSITION

BACKGROUND OF THE INVENTION

The present invention relates to a protecting and regenerating composition.

The present invention relates in particular to a composition comprising an association of a first cosmetically active ingredient comprising a vine shoot extract, and a second cosmetically active ingredient comprising a component of the ectoine type or family, named ectoine component. More particularly, said second ingredient is selected from ectoine, hydroxyectoine and mixtures thereof.

The present invention relates more particularly to a cosmetic composition for topical application to the skin which comprises such a composition.

The invention further relates to a method of cosmetic care comprising topical application to the skin of a person who wishes to effect cosmetic care with this composition.

STATE OF THE ART

The document WO 01/03713 discloses a process for the extraction of resveratrol and/or viniferine from dry vine shoots. It is pointed out that viniferine is the dimer of resveratrol. Said document also indicates that resveratrol is generally in the monomeric form, but also exists as an oligomer containing up to 4 monomers (page 1, lines 11 to 17).

The value of using dry shoots is emphasized because their yield of resveratrol and viniferine is much greater than that obtained with fresh shoots (page 2, line 31 to page 3, line 2).

Said document anticipates the possibility of obtaining grapevine extracts that are one thousand times more concentrated in respect of resveratrol than the commercialized extracts obtained from the vine, allowing the preparation of liquid, powder or tablet formulations having high resveratrol contents compatible with customary industrial applications for these products, and makes general mention in this context of the pharmaceutical, dietetic and cosmetic fields (page 5, lines 25 to 32 and claim 18).

Furthermore, it should be observed that the drying of the vine shoots described in said prior art document is carried out in the open air, but for a period of time not exceeding 4 months (Example 1: 4 months of drying; Example 2: 3 months of drying; Example 3: the longest drying is 3 months).

OBJECTS OF THE INVENTION

One main object of the present invention is to provide a novel composition comprising a synergistic association of active ingredients, and more particularly a cosmetic composition for topical application to the skin.

Another main object of the present invention is to provide such a composition from cosmetically acceptable active ingredients, i.e. active ingredients with no detectable toxicity on skin cells, which are available in large quantities at a reasonable price for use in the manufacture of cosmetic compositions on the cosmetic industrial scale.

Yet another main object of the present invention is to provide a composition with a limited content of resveratrol, favoring its oligomers.

SUMMARY OF THE INVENTION

The present invention simultaneously achieves the above objects in a simple manner that is easy to put into practice on the cosmetic industrial scale.

Thus, according to a first feature, the present invention provides a composition which comprises an association of a first cosmetically active ingredient comprising a dried vine shoot extract, and a second cosmetically active ingredient comprising a component of the ectoine type.

Within the framework of the invention, the expression "a component of the ectoine type" is understood as meaning an (S)-1,4,5,6-tetrahydropyrimidine-4-carboxylic acid which is unsubstituted or substituted by at least one C1-C6 lower alkyl radical, especially in the 2-position, and/or by at least one hydroxyl or methoxy group, especially in the 5-position, and its cosmetically acceptable salts or esters.

Preferably, said second ingredient is selected from ectoine, or (S)-1,4,5,6-tetrahydro-2-methylpyrimidine-4-carboxylic acid, and hydroxyectoine, or (S,S)-1,4,5,6-tetrahydro-5-hydroxy-2-methylpyrimidine-4-carboxylic acid, and their cosmetically acceptable salts or esters.

In another particular embodiment of the invention, this composition comprises from 0.1% to 20% by weight, preferably from 0.1% to 10% by weight, of the first ingredient; and from 0.1% to 20% by weight, preferably from 0.1% to 10% by weight, of the second ingredient, but the total of these two ingredients is advantageously less than or equal to 20% by weight, preferably less than 10% by weight, based on the total weight of the composition.

In yet another particular embodiment of the invention, the respective proportions by weight of the first ingredient and the second ingredient are between 1/10 and 10/1, particularly about 1/1.

In one particular embodiment of the invention, said second ingredient is a mixture of ectoine and hydroxyectoine in substantially equal proportions by weight.

According to a second feature, the present invention further relates to a cosmetic composition for topical application to the skin which comprises a composition as defined above or as resulting from the description below, associated with a cosmetically acceptable excipient.

In another variant, the composition comprises at least one other cosmetically active ingredient, especially another cosmetically active ingredient which has anti-ageing activity, particularly for preventing, correcting or slowing down the effects of skin ageing, e.g. vitamin A, vitamin E or vitamin C; or a cosmetically active ingredient which effects skin revitalization care, e.g. a madecassoside; or a cosmetically active ingredient which has a moisturizing effect, e.g. an ecdysteroid or a plant extract containing it, such as an extract of *Ajuga turkestanica*; or a cosmetically active ingredient for protecting against actinic radiation, e.g. a cosmetically acceptable physical or chemical sunscreen such as a methoxycinnamate.

According to a third feature, the present invention further relates to a method of cosmetic care which comprises the topical application, to the skin of a person who wishes to effect cosmetic care, of a composition as defined above or a cosmetic composition as defined above or as resulting from the description below.

In one particular variant of the method, said cosmetic care is selected from the group comprising anti-ageing care, particularly for preventing, correcting or slowing down the effects of skin ageing, and skin revitalization care. Its effects for combating skin ageing include mainly the combating of chronological or actinic ageing of the skin.

Within the framework of the invention, it has been possible to demonstrate a synergistic effect resulting from the association of the first cosmetically active ingredient comprising a vine shoot extract, and the second cosmetically active ingredient comprising a component of the ectoine type.

Within the framework of the invention, the vine shoot extract is any extract of vine shoots harvested from a vineyard. Shoots of any varieties of vine can be used, particular varieties being Merlot, Cabernet Franc, Gamay, Sirah, Sémillon and Sauvignon. Preferred vine shoots according to the invention are those of the Sémillon and/or Sauvignon variety.

In one particular embodiment, dried vine shoots are used. Dried vine shoots are understood as meaning shoots which have undergone a drying step so that their moisture content is advantageously below 20%, preferably below 5% by weight.

In one particular variant, the shoots are dried either naturally in the open air, in a dry place, or in an oven at a moderate temperature, e.g. not exceeding about 40° C., until the moisture content obtained in each case is below 20%, preferably below 5% by weight.

For example, the drying can be carried out naturally in the open air, in a dry place, by the drying process recommended in the above document WO 01/03713, which in particular comprises a drying period of at least two months, preferably of at least four months.

This natural drying in the open air favors the subsequent extraction of the active ingredients and especially the formation of resveratrol oligomers.

The vine shoot extract used within the framework of the invention is advantageously obtained by a process that ultimately affords an extract rich in polyphenolic molecules, and particularly resveratrol oligomers, which are sought within the framework of the invention for obtaining a cosmetic effect.

In one currently preferred embodiment of the invention, the extraction procedure mainly comprises the following steps:
 a) harvesting of the vine shoots from the vineyard;
 b) drying for a minimum period of 4 months;
 c) at least one extraction step with a polar organic solvent, e.g. a $C_1$-$C_6$ lower alcohol such as methanol, ethanol, propanol, isopropanol, butanol, pentanol or hexanol, either pure or mixed with water or an aqueous solution, or a ketone, particularly acetone, or a mixture of a ketone with water, to give a first polar solvent extract;
 d) at least one washing of said first polar solvent extract with an apolar organic solvent, such as hexane, to give a second extract, which can be used as such;
 e) optionally, and insofar as a more highly purified extract is sought, a purification is effected on a column, particularly a silica column, whereby the desired active substances, mainly polyphenolic substances and especially resveratrol oligomers, are fixed and then selectively eluted with an appropriate eluting mixture, e.g. ethyl acetate/hexane, especially in relative proportions of 80/20 v/v, to give a third highly purified extract, which can also be used as such; and
 f) optionally, the eluting solvent can be removed, especially by evaporation, to give a beige-colored powder, which constitutes the preferred final purified vine shoot extract according to the invention.

In one particular variant of the invention, said final powder can be resolubilized in an alcohol/water mixture, e.g. in relative proportions of 80/20 (v/v), and particularly in an 80/20 (v/v) mixture of butylene glycol/water.

This powder resolubilized in this 80/20 (v/v) mixture of alcohol/water affords at least about 1%, advantageously at least 10%, of viniferine, the dimer of resveratrol, in the final solution.

As regards the second cosmetically active ingredient comprising a component of the ectoine type, this is commercially available. For example, it is possible to use a product marketed by MERCK, e.g. under the trade name RONACARE® hydroine. This commercial product from MERCK is particularly valuable since the relative proportions of ectoine and hydroxyectoine are substantially equal (50-60% by weight of ectoine, 40-50% by weight of hydroxyectoine). This product also has a very good stability without the need to add antioxidant or preservative, and is of cosmetic grade.

Other objects, characteristics and advantages of the invention will become clearly apparent from the following explanatory description referring to the Examples according to the invention, which are given simply by way of illustration and cannot therefore in any way limit the scope of the invention.

In the Examples, all the percentages are given by weight, the temperature is in degrees Celsius and the pressure is atmospheric pressure, unless indicated otherwise.

BRIEF DESCRIPTION OF THE OF THE SEVERAL VIEWS OF THE DRAWINGS

FIG. 1 shows the results of the cell growth experiment described in Example 3 and performed with the aid of the commercial XTT test known as "Cell proliferation kit II" from BOEHRINGER, which respectively shows the cell growth kinetics for the untreated control, for the vine shoot extract I3 alone, for the "hydroine" product (RONACARE® from Merck) and for a combination of the extract I3 and hydroine, said kinetics being established from the cell growth measurements at 6 hours, 9 hours, 15 hours and 18 hours, plotted on the abscissa, the number of cells being plotted on the ordinate as a percentage relative to the number of cells at 6 hours, taken as 100%.

Figure 2:
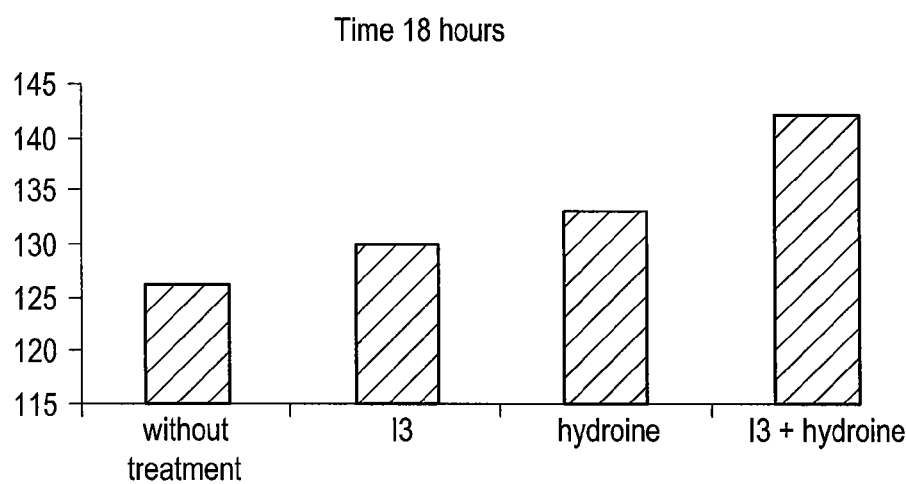

FIG. 2 is a curve derived from FIG. 1 which respectively shows in the form of bars, for the cell treatment time of 18 hours, the number of cells as a percentage for the untreated control, the extract I3, the "hydroine" product (RONACARE® from Merck) and finally the association according to the invention, in which the extract I3 and the hydroine product are combined, showing the synergistic effect of the association.

Figure 3:
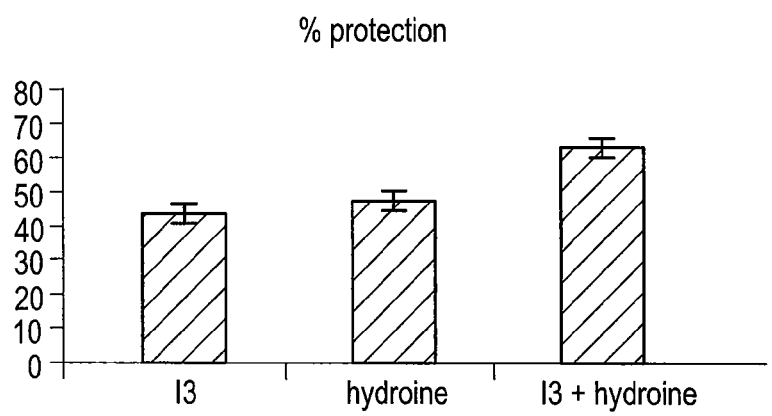

FIG. 3 shows the results of the anti-free radical protection test performed in Example 4, as the percentage protection, plotted on the ordinate, against the results in bar form respectively obtained for the extract I3, the "hydroine" product (RONACARE® from Merck) and the association of these two active ingredients, plotted on the abscissa, showing the unexpected superiority of the protection afforded by the association compared with each product taken individually.

DETAILED DESCRIPTION OF THE INVENTION

EXAMPLES OF THE INVENTION

Example 1

Process for The Preparation of a Vine Shoot Extract According to The Invention, Called I3

According to the invention, the extraction procedure mainly comprises the following steps:
 a) 1 kg of vine shoots of the Sauvignon variety is harvested in March-April from a vineyard situated to the south-east of Bordeaux;
 b) the collected vine shoots are dried in air, in a dry place, for a minimum period of 4 months, until the moisture content is below 5% by weight;
 c) to perform the extraction, the dried vine shoots are ground to a mean particle size of less than 4 mm. At least one extraction step is performed with a polar organic solvent, in this case acetone, in respective proportions by weight of ground shoots to solvent of at least 1/10, for a period of at least 20 hours, at room temperature or a temperature in the order of 30° C.; the solid residue is removed by filtration.

The acetone is evaporated from the acetone solution containing the solubilized extract to give a substantially dry, first crude extract, which is resolubilized in an ethanol/water mixture in proportions of 50/50 v/v, this crude extract, weighing around 30 g, requiring about 225 ml of said solvent. The water/ethanol solution containing the solubilized extract is maintained at room temperature or at a temperature of between 25° C. and 30° C. for one hour, with stirring, and the supernatants are separated off by filtration.

A purified extract in the solid state is obtained either by complete removal of the ethanol by evaporation, or by partial removal of the ethanol by evaporation to cause the precipitation of the purified extract, which is dried in conventional manner to give a purified extract in the form of a powder.

d) the above purified extract is then purified again by resolubilizing the resulting powder in an acetone/water mixture in relative proportions of 80/20 (v/v).

Hexane is added until a two-phase solution is obtained, the organic phase essentially consisting of hexane and the aqueous phase essentially comprising the acetone/water mixture. An extraction is thus performed with vigorous stirring at room temperature for a few minutes, e.g. about 10 min.

The mixture is left to stand so that the phases separate by decantation.

The aqueous phase containing the desired purified shoot extract is recovered.

e) the solvents are evaporated off to give a desired first purified shoot extract, which can be used as such and is called product I1 of the invention.

f) the product is advantageously purified on a silica column, whereby the desired active substances, mainly polyphenolic substances and especially resveratrol oligomers, are fixed. The silica column used in this Example is a column packed with type 60 silica from Merck. The polyphenolic substances fixed to the silica are then selectively eluted with an eluting solvent comprising an ethyl acetate/hexane mixture in relative proportions of 80/20 v/v, at a rate of 1 liter of solvent per gram of dry extract introduced into the column;

g) the eluting solvent is removed, especially by evaporation, to give a beige-colored powder, which constitutes a second final purified vine shoot extract according to the invention, called I2; and h) advantageously, this final powder I2 can be resolubilized in an alcohol/water mixture, in this case butylene glycol/water, in proportions of 80/20 (v/v), in order to facilitate its use in a composition, especially a cosmetic composition.

An analysis of this resolubilized powder according to the invention, called product or extract I3, shows that it contains about 68% of resveratrol oligomers, about 24% of which is viniferine.

Example 2

Composition According to The Invention

A composition is prepared which comprises 50% by weight of extract I3 obtained in Example 1, containing about 68% of resveratrol oligomers, and about 50% of components of the ectoine type obtained commercially, namely the hydroine product RONACARE® from MERCK.

This composition can be diluted in various proportions for carrying out the experiments forming the subject of the following Examples.

Example 3

Cell Growth Experiments

A—Cell Growth Model

The composition of Example 2 is to be tested in order to determine its influence on cell growth using the commercially available XTT test called "Cell proliferation kit II" from BOEHRINGER.

In this model the tetrazolium salt is converted to formazan—an orange compound detected at 450 nanometers by a spectrofluorimeter commercially available e.g. under the mark TECAN—by the dehydrogenases present in the mitochondrial respiratory chains. Thus, only living cells are capable of forming formazan.

The reaction is as follows:

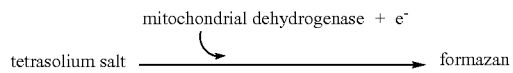

The cells are treated for a 24-hour period with the composition of Example 2 according to the invention, but diluted to a concentration of 1.56 µg/ml for each of the two active ingredients (i.e. 1.56 µg/ml of the composition of Example 2 and 1.56 µg/ml of RONACARE® from Merck), or, by way of comparison, with a solution of the composition of Example 2 or the hydroine product RONACARE® alone, the concentration being 3.52 µg/ml so as to have the same total concentration.

Measurements were made with the XTT test every three hours in order to follow the cell growth kinetics.

It should be noted that the first time taken into account, namely 6 hours after the start of the experiment, is considered to correspond to 100% of cells. It was not possible to take T0 or T3 because the standard deviations were too large, probably due to the perturbation associated with the changes of medium.

B—Treatment Protocol

Day D0

On day D0 immortalized transformed human keratinocytes of the HaCaT type, well known to those skilled in the art (see http:/cat.inist.fr/?aModele=afficheN&cpsidt=15688132 which cites the article of POZZI et al. in Journal of Endocrinal. Invest. 2004, vol 27, N°2, p 147-149), are inoculated into a 96-well microplate at a rate of 10,000 cells per well.

Day D24

On day D24 the treatments with the intended products mentioned above, at the indicated concentration, are started and the cell growth is followed.

C—Observations of the Effects of the Treatment at 3 Hours=T3, 6 Hours=T6, 9 Hours=T9, 15 Hours=T15 and 18 Hours=T18

At each step of the treatment indicated in the above title, the culture medium (complemented KSFM from Gibco) is removed.

The cells are treated either with the composition of Example 2 according to the invention, or with extract I3 alone, or with the commercial hydroine product RONACARE® from Merck.

To do this, dilutions of 1/16 and 1/32 are first prepared, under non-sterile conditions, from a 5% stock solution in DMSO (dimethyl sulfoxide) to give 3.12 mg/ml in the case where a single product is present, and 1.56 mg/ml for each product in the case of the mixture.

Dilutions of 1/1000 in the culture medium are then prepared under a hood to give a final concentration of 3.12 µg/ml for the mixture and 1.56 µg/ml for each ingredient.

Thus, for the test performed, the treatments were:
3.12 µg/ml for the extract I3 of Example 1;
3.12 µg/ml for the hydroine product RONACARE® from MERCK;
in the case of the composition of Example 2 of the invention comprising the mixture, 1.56 jig/ml for I3 of Example 1 and 1.56 µg/ml for the hydroine product RONACARE® from MERCK.

D—Development of the Test

To develop the test, the culture medium is removed by turning the microplate over.

The cells are rinsed once: for 200 µl/well, the cells are rinsed with PBS at 37° C.

XTT solution at a concentration of 0.2 mg/ml (1/5 dilution of the 1 mg/ml stock solution), prepared for immediate use in complemented KSFM medium, is added at a rate of 100 µl/well.

A blank without cells is prepared.

The microplate is wrapped in aluminum paper and incubated for 3 hours at 37° C. in an oven with 5% of $CO_2$.

At the end of the 3-hour incubation, the optical densities (OD) at 450 nm are read off on a commercially available Tecan spectrophotometer.

The results obtained are expressed below:

E—Expression of the Results

The treatment time of 6 hours=T6 is considered to correspond to 100% of cells in the wells.

The percentage viability is given by the following formula:

% viability=($OD$×100)/($OD$ control–100)

Results

The results are expressed in Table I below:

TABLE I

| Treatment time at D24 | % viability without treatment | % viability with I3 of Example 1 | % viability with RONACARE ® hydroine | % viability with the composition of Example 2 of the invention |
|---|---|---|---|---|
| 6 hours | 100 | 100 | 100 | 100 |
| 9 hours | 106 | 108 | 108 | 113 |
| 15 hours | 110 | 112 | 111 | 127 |
| 18 hours | 126 | 130 | 133 | 142 |

The results obtained are given in the form of a curve in FIG. 1.

It is seen from these results that for the cells treated with the composition of Example 2 according to the invention, comprising an association of the product I3 of the invention, containing a predominance of resveratrol oligomers, with a product of the hydroine type, a more sustained growth is obtained than with the untreated cells or with the cells treated only with the product I3 of Example 1 or the hydroine-type product RONACARE® from Merck.

It should be noted, however, that the product I3 of Example 1 and the hydroine-type product individually exhibit a low activity.

Furthermore, by virtue of the composition according to the invention, the cell growth dynamics are much better at the same 18-hour finishing point.

FIG. 2 represents a comparison of the results for the treatment time of 18 hours and clearly shows that the association according to the invention has a synergistic action, which is totally unexpected for those skilled in the art.

Example 4

Anti-Free Radical Protection Test

Model: 3D Test (AES Laboratoire)

This test makes it possible to demonstrate the DNA-protecting effect of a molecule against hydroxyl radicals generated by hydrogen peroxide.

To characterize a molecule or a mixture having antioxidant or anti-free radical properties, and hence to protect a human cell from the oxidative damage due to reactive oxygenated species (ROS), 3 criteria established by Barry Halliwell have to be taken into account:

the molecule must prove that it is active in the cell; a purely chemical test will suggest but not demonstrate it;

the molecule must be effective against a biological oxidant, i.e. an oxidant present in the cells. Certain antioxidants have a specific protective activity against certain oxidants; and the concentrations of oxidant used must be compatible with those which can be used in vivo.

These comments by Barry Halliwell, an oxidant specialist, are taken from the article published in 1995 in the journal Biochemical Pharmacology (volume 49, 1341-1348), entitled "Antioxidant characterization—Methodology and Mechanism".

The 3D TEST therefore makes it possible to demonstrate the DNA-protecting effect of a molecule against hydroxyl radicals generated by hydrogen peroxide in the presence of $FeCl_2$.

Moreover, the 3D TEST on cells satisfies Barry Halliwell's criteria perfectly.

Principle:

S.F.R.I. and the Toxico-Resistance team of I.P.B.S. CNRS, Toulouse, have developed a system for detecting damage (3D TEST) on DNA collected on a microplate (Analytical Biochemistry, 1995, 232, 37-42).

The DNA is adsorbed onto sensitized wells and then incubated with oxidizing agents (hydrogen peroxide +iron). The damage generated is recognized and then repaired with the specific protein complexes present in purified cell extracts of human origin. The repair of the lesions involves a lesion excision phase and then a resynthesis of the DNA fragment or the excised bases.

During the reparative synthesis step, modified nucleotides (biotin-coupled dUTP) are incorporated into the DNA. These biotinylated nucleotides are then recognized by a peroxidase-coupled avidine molecule. A chemoluminescent peroxidase substrate is then added and the signal emitted is measured with a luminometer (Spectrafluorplus, Tecan). The intensity of the measured signal, hereafter designated by RLU, is a function of the number of repaired lesions on the DNA. A dose effect is observed within the limits of 1 to 15 lesions per 6 kilobases for the majority of the lesions.

This system is capable of repairing all types of lesions because the different DNA lesion repair pathways (NER and BER) are present and active in the cell extracts prepared and used for this study. The oxidative damage is therefore recognized in this system.

Materials and Methods

1. Materials

The reagents used have been described in the article Analytical Biochemistry, 1995, 232, 37-42.

The chemoluminescent signal is detected with a Spectrafluorplus luminometer (Tecan).

2. In Vitro 3D TEST Methods 2.1 Dilutions of the Test Samples

The samples of shoot extract I3 and hydroine are dissolved in methanol at a stock concentration of 50 mg/ml.

The concentrations studied are prepared by successive dilution of the stock solution in ultrapure water. All the dilutions are prepared at twice the concentration so as to give the desired concentrations after the addition of one volume of an oxidizing solution of hydrogen peroxide +FeCl$_2$.

To verify the specificity of the decrease in the repair signal, the same dilutions (iX) were incubated under the same conditions on DNA damaged by hydrogen peroxide +FeCl$_2$. A dilution will only exhibit a protective effect if a drop in the repair signal in the presence of oxidant is observed and the absence of a significant modification of the signal on the previously damaged DNA is observed. An inhibition of the repair signal on the damaged DNA can be explained e.g. by a direct interaction of the sample with the DNA, which would have the effect of blocking access to the lesions by the protein repair complexes.

2.2 Adsorption of the Target DNA in the Microplate Wells

Ultrapurified plasmid DNA (pBS) (predominant supercoiled form) is brought into contact with the sensitized wells for 30 minutes at 30° C., with gentle shaking. Under these conditions, the adsorption of the DNA is quantitative.

A positive repair control, consisting of a plasmid DNA previously damaged with H-$_2$O$_2$+FeCl$_2$, is added.

2.3 Search for a Protective Effect of the Samples Against Reactive Oxygen Species The hydroxyl radical OH° is produced by Fenton's reaction (hydrogen peroxide+FeCl$_2$).

Fenton's reaction: Carried out by adding a mixture of H$_2$O$_2$+FeCl$_2$ $$H_2O_2 + Fe^{2+} \rightarrow Fe^{3+} + OH^- + OH°$$

These radicals, which are powerful electrophiles, have a very short life (in the order of $10^{-9}$ second). They therefore react very rapidly with the DNA bases and produce different kinds of damage, such as modifications or losses of bases. These very genotoxic lesions are recognized by the repair system.

The hydrogen peroxide is prepared at a concentration of 4 mM in ultrapure water (MilliQ grade from Millipore). The FeCl$_2$ is prepared at a concentration of 2 μM in ultrapure water. The two solutions are diluted in equal volumes immediately before use.

This solution is mixed immediately before use with an equal volume of the different dilutions of the test samples. 50 μl of the mixture are added to the wells containing the adsorbed plasmid DNA. The whole is then incubated for 30 minutes at 30° C., with gentle shaking.

A rinsing step is then carried out so as to retain only the DNA that has been more or less damaged by the oxidant.

The lesion repair step is then carried out with the specific repair complexes. During the phase of resynthesis of the excised DNA strand, a biotin-labeled nucleotide is incorporated into the DNA (incubation for 3 hours at 30° C., without shaking).

A rinsing step is then carried out in order to remove the biotin not incorporated in the DNA.

This is followed by a step for recognition of the biotin by an avidine molecule coupled with a peroxidase molecule (15 minutes at 30° C., with gentle shaking).

A further rinsing step is then carried out in order to remove the avidine coupled with a peroxidase molecule that is not fixed to the biotin.

Finally, a step for developing the repair reaction is performed by adding a chemoluminescent peroxidase substrate (5 minutes at 30° C., with gentle shaking) and then reading off the luminescence.

Interpretation of the Results

The visualization of the results is improved by expressing them as a percentage protection or percentage inhibition of the formation of oxidative damage on the DNA. A value of 0% corresponds to the repair signal for DNA damaged by the oxidant alone.

The percentage protection in the presence of ROS is calculated as the relative drop in the damaging effect due to OH° or $^1O_2$ radicals, i.e.:

$$\frac{[RLU \text{ oxidant alone}] - [RLU(\text{oxidant} + \text{sample})]}{[RLU \text{ oxidant alone}]} \times 100$$

A non-specific inhibition (in the absence of ROS) of the repair signal can sometimes be observed. This may be due to a direct interaction of the compound with the DNA (desorption of the DNA from the well, non-specific association with the DNA which will mask the lesions from the repair proteins, etc.). A control, consisting in incubating the tested agents with previously damaged DNA, is therefore added. A decrease in the signal under this condition reflects a non-specific inhibition of the compound that is independent of its possible anti-free radical properties.

An inhibition of the repair in the presence of ROS can be the consequence of:
- a genuine protection;
- a decrease in the efficacy of the repair of a damaged DNA due to a direct interaction of the test molecule with the DNA or the treated microplate; or
- the simultaneous occurrence of these 2 phenomena.

The non-specific inhibition is therefore evaluated. It is calculated from the results obtained for the samples incubated on the previously damaged DNA.

The specific inhibition or specific protection is equal to the difference between the inhibition in the presence of ROS and the non-specific inhibition. It reflects the anti-free radical activity due to the molecule alone.

TABLE II

Anti-free radical protection test

| Sample | % protection |
|---|---|
| Solvent control | — |
| I3 | 43 |
| RONACARE ® hydroine | 47 |
| I3 + RONACARE ® hydroine (invention) | 62 |

The samples of shoot extract I3 and hydroine exhibit a protective activity against free radicals. The efficacy of protection is increased by about 40% in the treatment with the composition of the invention.

Hence there is indeed a synergism between the two molecules.

The recommended doses are 0.1% to 10% of the 1/1 mixture of shoot extract/hydroine component.

It is apparent from Table II and attached FIG. 3 that each sample of product I3 and hydroine product exhibits a protective activity against free radicals.

By contrast, the composition according to the invention, in which the product I3 and the hydroine product are combined, affords an approximately 40% increase in the efficacy of protection, demonstrating a synergistic effect between the two molecules which is totally unexpected for those skilled in the art.

Example 5

Evidencing The Anti-Free Radical Activity of The Association Accroding to The Invention The oxygen free radical species are produced within the skin by different aggressive factors, such as UV rays, stresses and inflammatory reactions.

These oxidizing molecules attack the skin constituents, notably lipids, proteins, polysaccharides and cellular DNA, perturbating the biological functions. The test used herein to evidence the protecting effect of the association of the shoot vine extract and of the component of ectoine type, according to the invention, after its application onto the skin is based on that described in the publication entitled "A new method for assessing in vivo, in human subjects, the basal or UV-induced peroxydation of the stratum corneum. Application to test the efficacy of free-radical-scavenging products", from P. Girard, L. Lempereur, P. Buche and L. Violin, in the review Curr. Probl. Dermatol., 1998, 26, 99-107.

The principle of this test is based on the reaction of the oxygen free-radicals present at the surface of the skin with a marker constituted by DCF(H)-DA (2'7' dichlorofluorescin diacetate) which leads to a fluorescent product, noted DCF*, which fluorescence is measured with a fluorometer. The measure of this fluorescence enables to quantify the presence of free-radicals and therefore of the degree of activity of the protecting product.

30 healthy volunteers of the Caucasian type and of female sex have been selected.

The product to be tested is applied onto a zone of the internal part of the fore-arm at an amount of 2 µl/cm² by application. It is performed four applications spaced apart from 2 hours each.

The tested person is authorized thereafter to use her usual cleaning products at the exclusion of any skin care product.

24 hours after the first application of the tested product, it is performed a stripping with the help of standard transparent adhesive disks, available on the market under the trademark D-Squamesg®.

The amount of corneocytes thus removed is evaluated by measure of the infrared light transmitted through the D-Squames® with a device available on the market named Squameter, to take into account the number of squamae in the statistical analysis of the measured results.

The different disks D-Squames® are then incubated within a buffer-phosphate solution 66 mM at a pH of 7.4 during 32 hours at 37° C., containing DCF*. The fluorescence of the solution is quantitatively measured in each case after incubation with a flurometer of the trademark Fluroskan Ascent (Labsystems).

The following products have been tested:

Product 1 (of the invention): emulsion (cream) containing, by weight, 1% of extract I3 and 1% of hydroine RONACARE® of the company MERCK, herein after "hydroine", Product 2 (of the invention): lotion containing 1 % of extract I3 and 1.5 % of hydroine, Product 3: emulsion containing polyphenols of grape pips, Product 4: emulsion containing 0.5 of idebenone, well-known anti-oxidizing agent, Product 5: emulsion containing 1% of idebenone.

The results of measures of fluorescence are reported in the here below table III:

TABLE III

|  | Fluorescence | Comparison to TNT (%) |
|---|---|---|
| Product 1 (of the invention) | 106.6 | −19% |
| Product 2 (of the invention) | 101.0 | −23% |
| Product 3 | 121.1 | NS |
| Product 4 | 126.5 | NS |
| Product 5 | 114.7 | −13% |
| Control (subject not treated) ("TNT") | 131.7 |  |

S ($<0.01$)

Thus, fluorescence being directly correlated to the amount of present free-radicals, it clearly appears according to the here above results that the amount of free-radicals is very significantly lowered in the presence of the invention products. Therefore, the invention products provide a well better anti-radical action, in vivo.

Various Examples of cosmetic formulations of the composition according to the invention will be given below, the different ingredients being formulated in conventional manner by those skilled in the art.

Example 6

| Cosmetic composition in the form of a cream according to the invention | |
|---|---|
| Steareth-21 (Brij 721) | 2.5% |
| Glyceryl stearate (Tegin) | 1.1 |
| Stearyl alcohol | 5 |
| Glycerol tricaprate/caprylate | 11.5 |
| Butylene glycol | 3 |
| Glycerol | 2 |
| Preservative | 0.5 |
| Perfume concentrate | 0.5 |
| Water | 62.4 |
| Composition of Example 2 | 5 |
| Octyl methoxycinnamate | 7.5 |

Example 7

| Cosmetic composition in the form of a gel | |
|---|---|
| Glycerol | 3% |
| AMPS polymer (Sepigel 305) | 3 |
| Hydrogenated castor oil (Cremophor CO-60) | 2 |
| Polyethylene glycol | 1.5 |
| Preservative | 0.5 |
| Perfume concentrate | 0.3 |

-continued

| Cosmetic composition in the form of a gel | |
|---|---|
| Water | 85.7 |
| Composition of Example 2 | 3 |
| Benzophenone 4 | 1 |

Example 8

| Cosmetic composition in the form of a lotion | |
|---|---|
| Butylene glycol | 3% |
| EDTA | 0.1 |
| Solubilizer | 1 |
| Perfume concentrate | 0.3 |
| Alcohol | 5 |
| Water | 80.47 |
| Composition of Example 2 | 10 |
| Benzophenone 4 | 0.13 |

What is claimed is:

1. A composition which comprises an association of a first cosmetically active ingredient comprising a dried vine shoot extract, wherein said vine shoots have been dried until the moisture content is below 5% by weight, thereby promoting content in resveratrol oligomers, among which at least 1% by weight in viniferine with respect to the resveratrol oligomers content, and a second cosmetically active ingredient comprising an ectoine component.

2. The composition of claim 1, wherein the ectoine component is an (S)-1,4,5,6-tetrahydropyrimidine-4-carboxylic acid which is unsubstituted or substituted by at least one C1-C6 lower alkyl radical, especially in the 2-position, and/or by at least one hydroxyl or methoxy group, especially in the 5-position, and its cosmetically acceptable salts and esters.

3. The composition of claim 1, wherein the second ingredient is selected from ectoine and hydroxyectoine and their cosmetically acceptable salts or esters.

4. The composition of claim 1, wherein the second ingredient is a mixture of ectoine and hydroxyectoine in substantially equal proportions by weight.

5. The composition of claim 1, which comprises from 0.1% to 20% by weight of said first ingredient; and from 0.1% to 20% by weight of said second ingredient.

6. The composition of claim 1, which comprises from 0.1% to 10% by weight of said first ingredient; and from 0.1% to 10% by weight of said second ingredient.

7. The composition of claim 1, wherein the total of the first ingredient and of the second ingredient is less than or equal to 20% by weight.

8. The composition of claim 1, wherein the respective proportions by weight of said first ingredient and said second ingredient are between 1/10 and 10/1, particularly about 1/1.

9. A cosmetic composition for topical application to the skin which comprises an association of a first cosmetically active ingredient comprising a dried vine shoot extract, wherein said vine shoots have been dried until the moisture content is below 5% by weight, thereby promoting content in resveratrol oligomers, among which at least 1% by weight in viniferine with respect to the resveratrol oligomers content and of a second cosmetically active ingredient comprising an ectoine component, with a cosmetically acceptable excipient.

10. The composition of claim 9, wherein the ectoine component is an (S)-1,4,5,6-tetrahydropyrimidine-4-carboxylic acid which is unsubstituted or substituted by at least one C1-C6 lower alkyl radical, especially in the 2-position, and/or by at least one hydroxyl or methoxy group, especially in the 5-position, and its cosmetically acceptable salts and esters.

11. The composition of claim 9, wherein the second ingredient is selected from ectoine and hydroxyectoine and their cosmetically acceptable salts or esters.

12. The composition of claim 9, which comprises from 0.1% to 20% by weight of said first ingredient; and from 0.1% to 20% by weight of said second ingredient.

13. The composition of claim 9, which comprises at least one further cosmetically active ingredient, selected from the group consisting of a cosmetically active ingredient having an anti-ageing activity; a cosmetically active ingredient having an effect on skin revitalization; a cosmetically active ingredient having a moisturizing effect; and a cosmetically active ingredient for protecting against actinic radiation.

14. The composition of claim 13, wherein said cosmetically active ingredient having an anti-ageing activity is selected from vitamin A, vitamin E and vitamin C; said cosmetically active ingredient having effect on skin revitalization is a madecassoside; said cosmetically active ingredient which has a moisturizing effect is selected from an ecdysteroid, a plant extract containing ecdysteroid, and an extract of *Ajuga turkestanica*; said cosmetically active ingredient for protecting against actinic radiation, is selected from a cosmetically acceptable physical sunscreen, and a cosmetically acceptable chemical sunscreen.

15. The composition of claim 14, wherein said cosmetically acceptable chemical sunscreen is methoxycinnamate.

16. The composition of claim 9, wherein the content in viniferine is at least 10% by weight with respect to the resveratrol oligomers content.

17. The composition of claim 9, wherein the content in resveratrol oligomers is of about 68% by weight, among which about 24% by weight is viniferine with respect to the resveratrol oligomers content.

18. A method of cosmetic care which comprises the topical application, to the skin of a person who wishes to effect cosmetic care, of a cosmetic composition for topical application to the skin which comprises an association of a first cosmetically active ingredient comprising a dried vine shoot extract, and of a second cosmetically active ingredient comprising an ectoine component, with a cosmetically acceptable excipient.

19. The method of claim 18, wherein the ectoine component is an (S)-1,4,5,6-tetrahydropyrimidine-4-carboxylic acid which is unsubstituted or substituted by at least one substituent selected from a C1-C6 lower alkyl radical, an hydroxyl and a methoxy group, and its cosmetically acceptable salts and esters.

20. The method of claim 18, wherein the second ingredient is selected from ectoine and hydroxyectoine and their cosmetically acceptable salts or esters.

21. The method of claim 18, which comprises from 0.1% to 20% by weight of said first ingredient; and from 0.1% to 20% by weight of said second ingredient.

22. The method of claim 18, wherein said cosmetic composition comprises at least one further cosmetically active ingredient, selected from the group consisting of a cosmetically active ingredient having an anti-ageing activity; a cosmetically active ingredient having an effect on skin revitalization; a cosmetically active ingredient having a moisturizing effect; and a cosmetically active ingredient for protecting against actinic radiation.

23. The method of claim 22, wherein said cosmetically active ingredient having an anti-ageing activity is selected from vitamin A, vitamin E and vitamin C; said cosmetically active ingredient having effect on skin revitalization is a madecassoside; said cosmetically active ingredient which has a moisturizing effect is selected from an ecdysteroid, a plant extract containing ecdysteroid, and an extract of *Ajuga turkestanica*; said cosmetically active ingredient for protecting against actinic radiation, is selected from a cosmetically acceptable physical sunscreen, and a cosmetically acceptable chemical sunscreen.

24. The method as claimed in claim 18, wherein the cosmetic care is selected from the group consisting of an anti-ageing care, and skin revitalization care.

25. The method of claim 18, wherein the content in viniferine is at least 10% by weight with respect to the resveratrol oligomers content.

26. The method of claim 18, wherein the content in resveratrol oligomers is of about 68% by weight, among which about 24% by weight is viniferine with respect to the resveratrol oligomers content.

* * * * *